(12) United States Patent
Baroud

(10) Patent No.: US 8,710,852 B2
(45) Date of Patent: Apr. 29, 2014

(54) METHOD AND APPARATUS FOR MONITORING AND/OR CONTROLLING THE CURING OF CEMENTS USED IN MEDICAL PROCEDURES

(71) Applicant: Societe de Commercialisation des Products de la Recherche Appliquée SOCPRA Sciences et Génie S.E.C., Sherbrooke (CA)

(72) Inventor: Gamal Baroud, Canton-de-Hatley (CA)

(73) Assignee: SOCPRA Sciences et Genie S.E.C., Sherbrooke (CA)

( * ) Notice: Subject to any disclaimer, the term of this patent is extended or adjusted under 35 U.S.C. 154(b) by 0 days.

(21) Appl. No.: 14/016,734

(22) Filed: Sep. 3, 2013

(65) Prior Publication Data

US 2014/0009173 A1    Jan. 9, 2014

Related U.S. Application Data

(60) Division of application No. 12/570,515, filed on Sep. 30, 2009, now Pat. No. 8,552,745, which is a continuation of application No. PCT/CA2008/000589, filed on Mar. 31, 2008.

(60) Provisional application No. 60/907,381, filed on Mar. 30, 2007.

(51) Int. Cl.
*G01R 27/26* (2006.01)

(52) U.S. Cl.
USPC ............................................ 324/663; 324/671

(58) Field of Classification Search
USPC ................. 324/663, 658, 649, 600, 671, 341; 606/93, 86 R, 53, 1
See application file for complete search history.

(56) References Cited

U.S. PATENT DOCUMENTS

| | | | |
|---|---|---|---|
| 3,365,936 A | | 1/1968 | Hubin et al. |
| 4,012,197 A | * | 3/1977 | Howarth .................... 436/150 |
| 4,120,166 A | * | 10/1978 | Brooks, Jr. .................. 405/225 |
| 4,236,109 A | | 11/1980 | Ingle, Jr. |
| 4,399,100 A | | 8/1983 | Zsolnay et al. |
| 4,423,371 A | | 12/1983 | Senturia et al. |
| 4,554,686 A | | 11/1985 | Baker |
| 4,854,716 A | | 8/1989 | Ziemann et al. |
| 4,891,591 A | | 1/1990 | Johnston et al. |
| 5,051,482 A | | 9/1991 | Tepic |
| 5,145,250 A | | 9/1992 | Plank et al. |

(Continued)

FOREIGN PATENT DOCUMENTS

| | | |
|---|---|---|
| CA | 2603010 | 10/2006 |
| DE | 100 08 481 A1 | 9/2001 |

*Primary Examiner* — Hoai-An D Nguyen
(74) *Attorney, Agent, or Firm* — Norton Rose Fulbright Canada LLP

(57) ABSTRACT

An apparatus for determining an initiation point of cement curing, with a vessel for containing at least a portion of freshly mixed cement, means for passing an electric signal through the cement, means for detecting an abrupt change in a dielectric or electric property of the cement as a result of the electric signal and a display unit for displaying the initiation point of polymerization of the cement from the abrupt change in the dielectric or electric property detected, the change in the dielectric or electric property being a phase shift in the electric signal passed through the cement or a change in capacitive properties of the cement or a change in resistivity of the cement.

18 Claims, 15 Drawing Sheets

(56) References Cited

U.S. PATENT DOCUMENTS

| | | |
|---|---|---|
| 5,211,477 A | 5/1993 | Li |
| 5,279,149 A | 1/1994 | Williams et al. |
| 5,412,990 A | 5/1995 | D'Angelo et al. |
| 5,436,565 A | 7/1995 | Gammell |
| 5,443,182 A | 8/1995 | Tanaka et al. |
| 5,545,460 A | 8/1996 | Tanaka et al. |
| 5,804,725 A | 9/1998 | Posakony et al. |
| 5,872,447 A | 2/1999 | Hager, III |
| 5,898,309 A | 4/1999 | Becker et al. |
| 5,992,223 A | 11/1999 | Sabins et al. |
| 6,005,163 A | 12/1999 | Tepic |
| 6,409,972 B1 | 6/2002 | Chan |
| 6,605,651 B1 | 8/2003 | Stangel et al. |
| 6,719,761 B1 | 4/2004 | Reiley et al. |
| 6,804,346 B1 | 10/2004 | Mewhinney |
| 6,814,736 B2 | 11/2004 | Reiley et al. |
| 6,819,121 B1 | 11/2004 | Hager, III et al. |
| 6,854,349 B2 | 2/2005 | Brandhorst et al. |
| 6,941,819 B1 | 9/2005 | Maki, Jr. et al. |
| 7,225,682 B2 | 6/2007 | Shtakelberg et al. |
| 7,559,932 B2 | 7/2009 | Truckai et al. |
| 2006/0000284 A1 | 1/2006 | Sherman et al. |
| 2006/0122621 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |
| 2006/0198419 A1 | 9/2006 | Intermill et al. |
| 2006/0236794 A1 | 10/2006 | Sherman et al. |
| 2007/0027230 A1 | 2/2007 | Beyar et al. |
| 2007/0118144 A1 | 5/2007 | Truckai et al. |
| 2007/0154874 A1 | 7/2007 | Sherman et al. |
| 2007/0162043 A1 | 7/2007 | Truckai et al. |
| 2007/0191858 A1 | 8/2007 | Truckai et al. |
| 2007/0233147 A1 | 10/2007 | Vendrely et al. |
| 2007/0233148 A1 | 10/2007 | Truckai et al. |
| 2008/0027456 A1 | 1/2008 | Truckai et al. |
| 2009/0084978 A1 | 4/2009 | Chandler et al. |
| 2010/0110436 A1 | 5/2010 | Chandler et al. |

\* cited by examiner

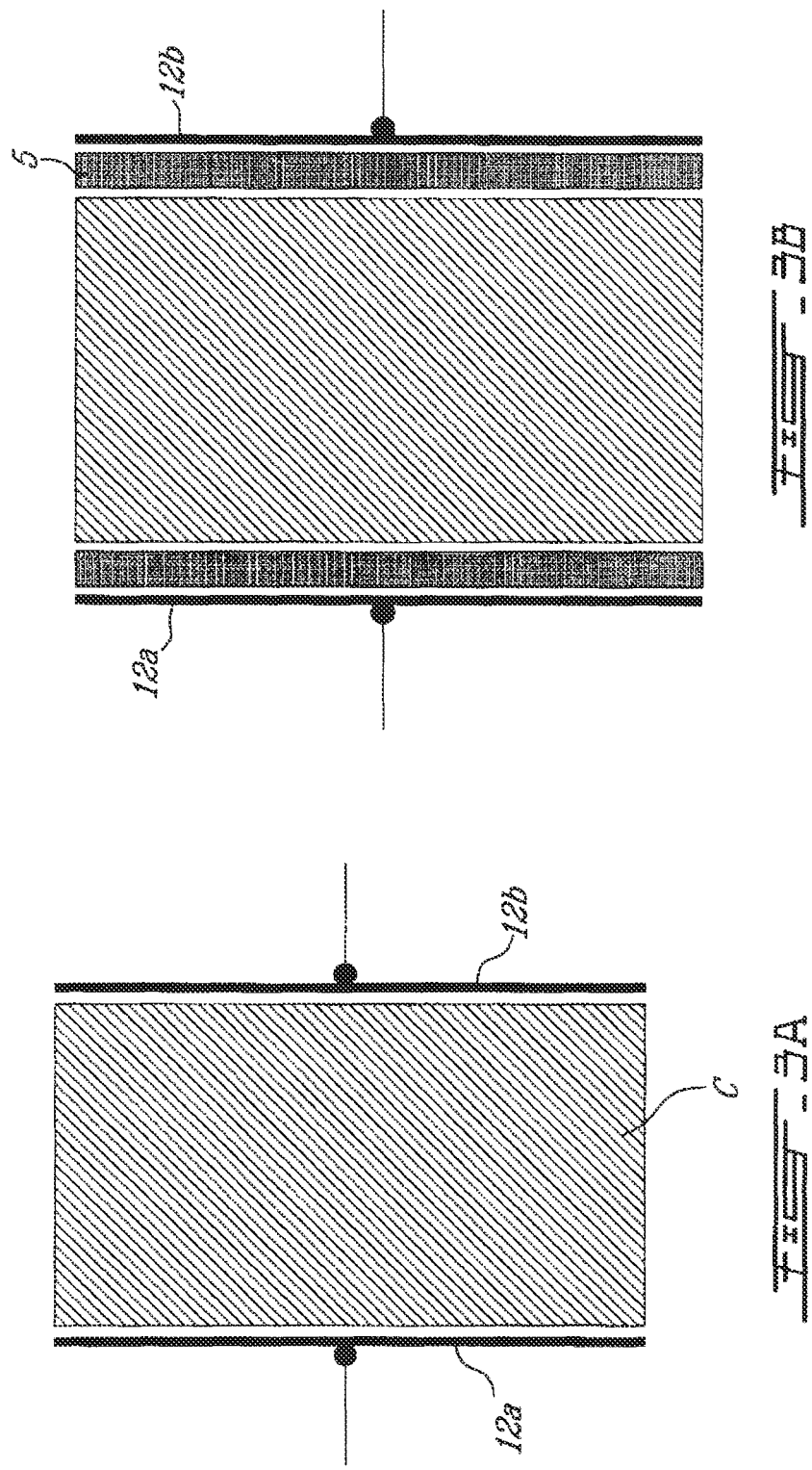

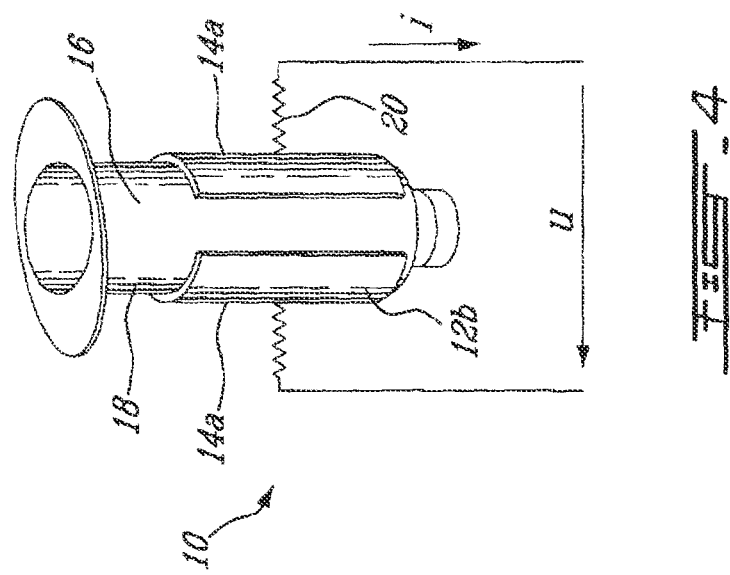
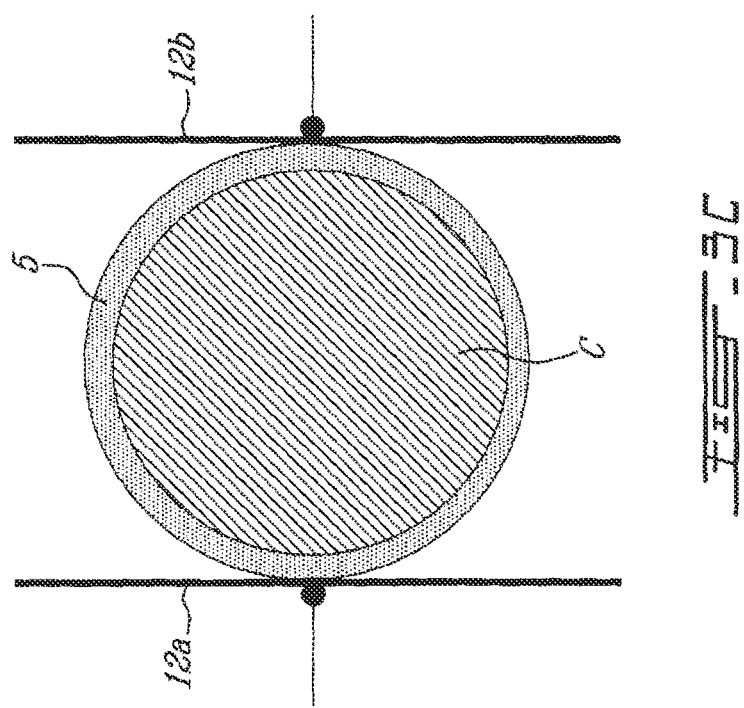

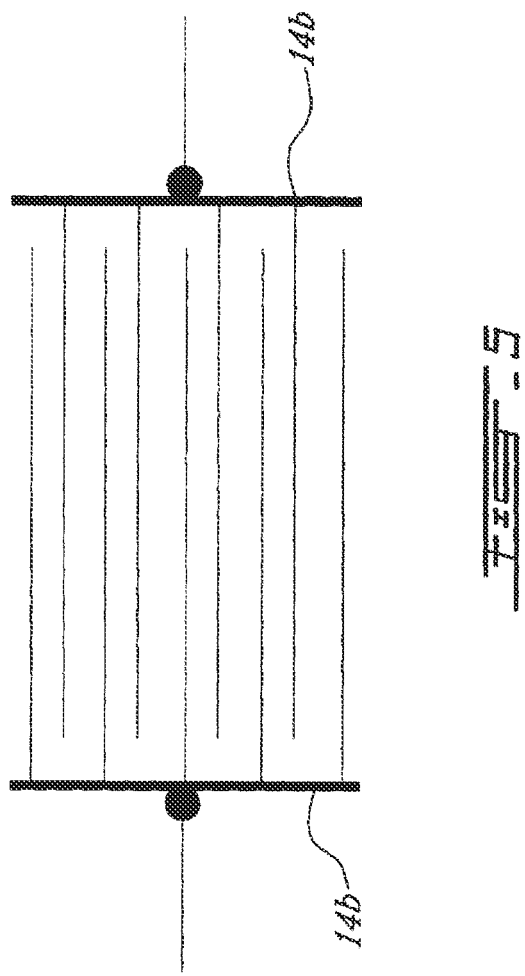

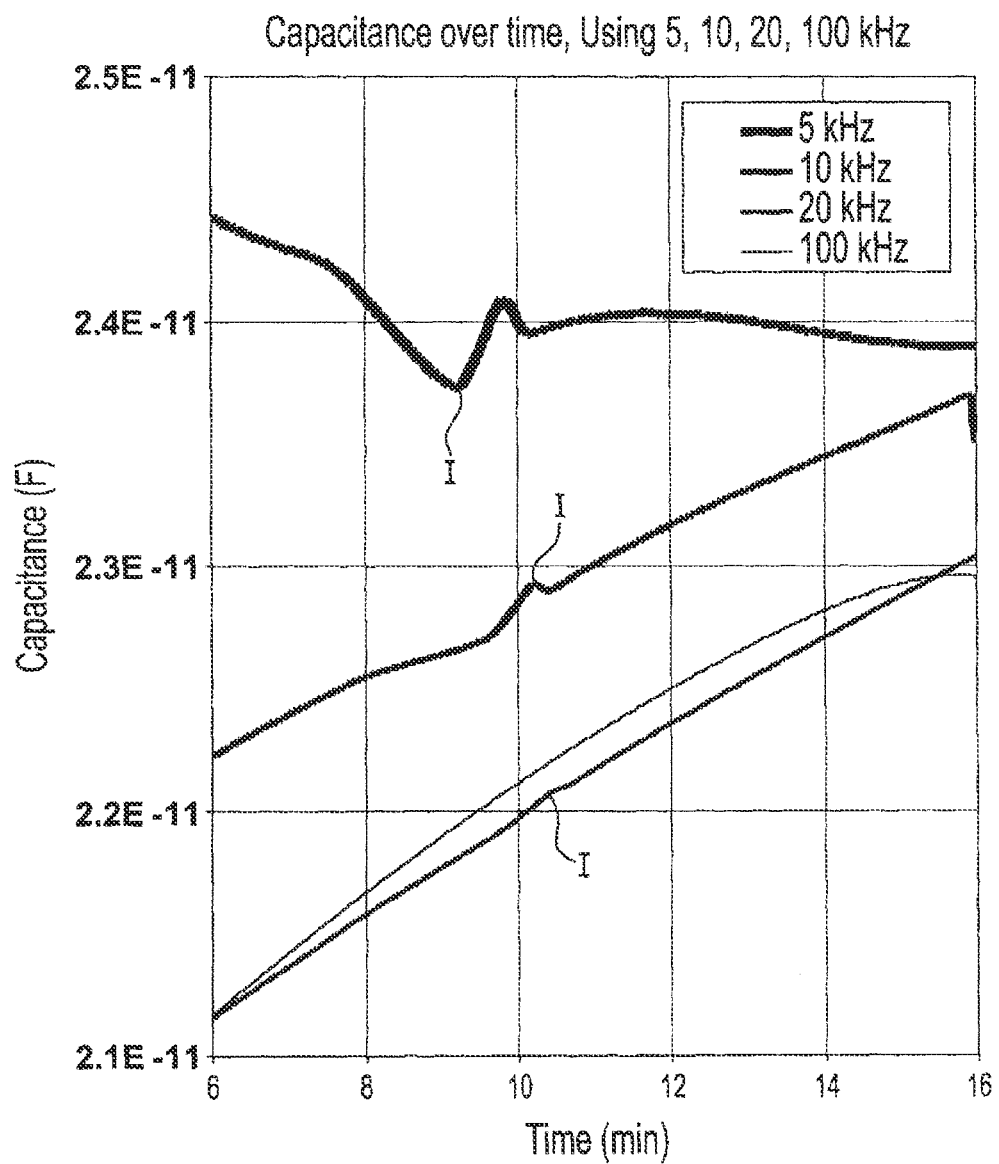

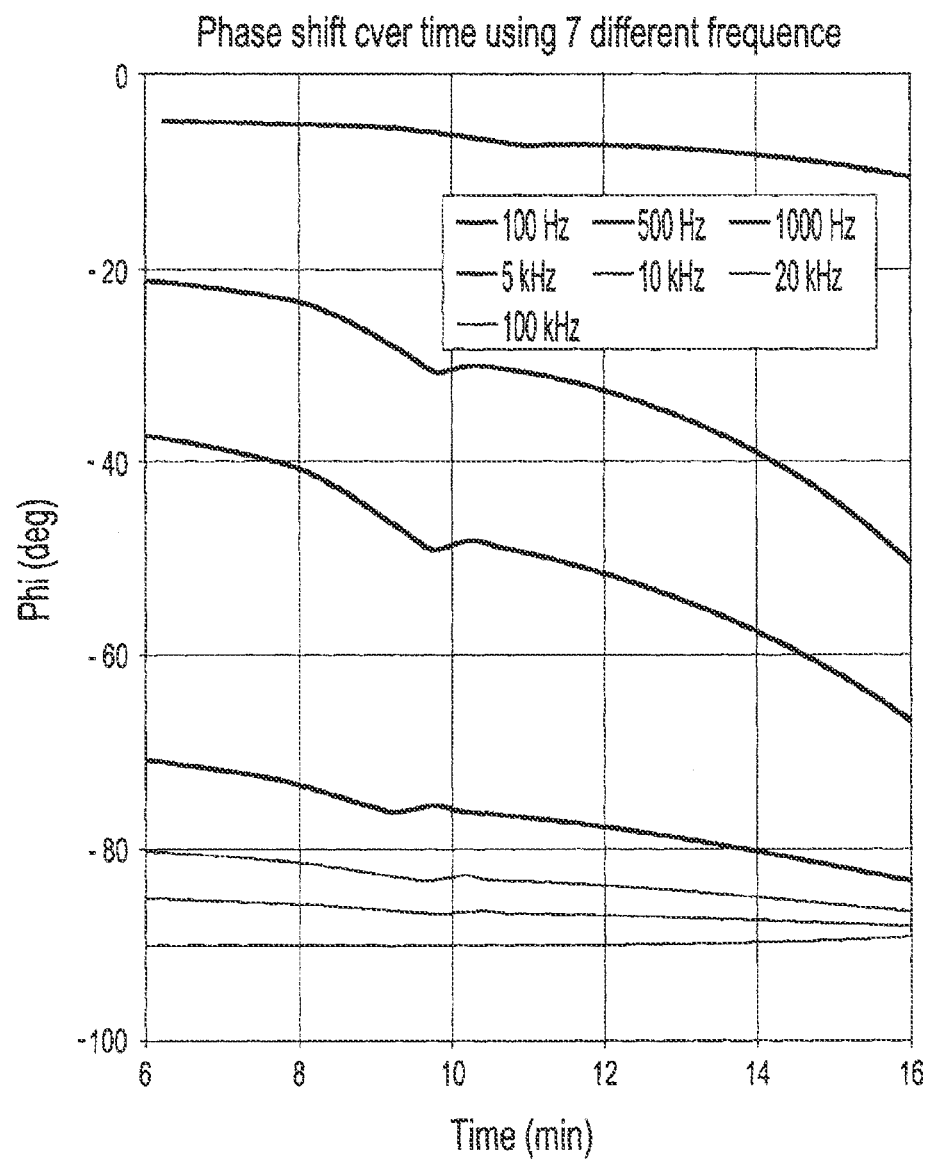

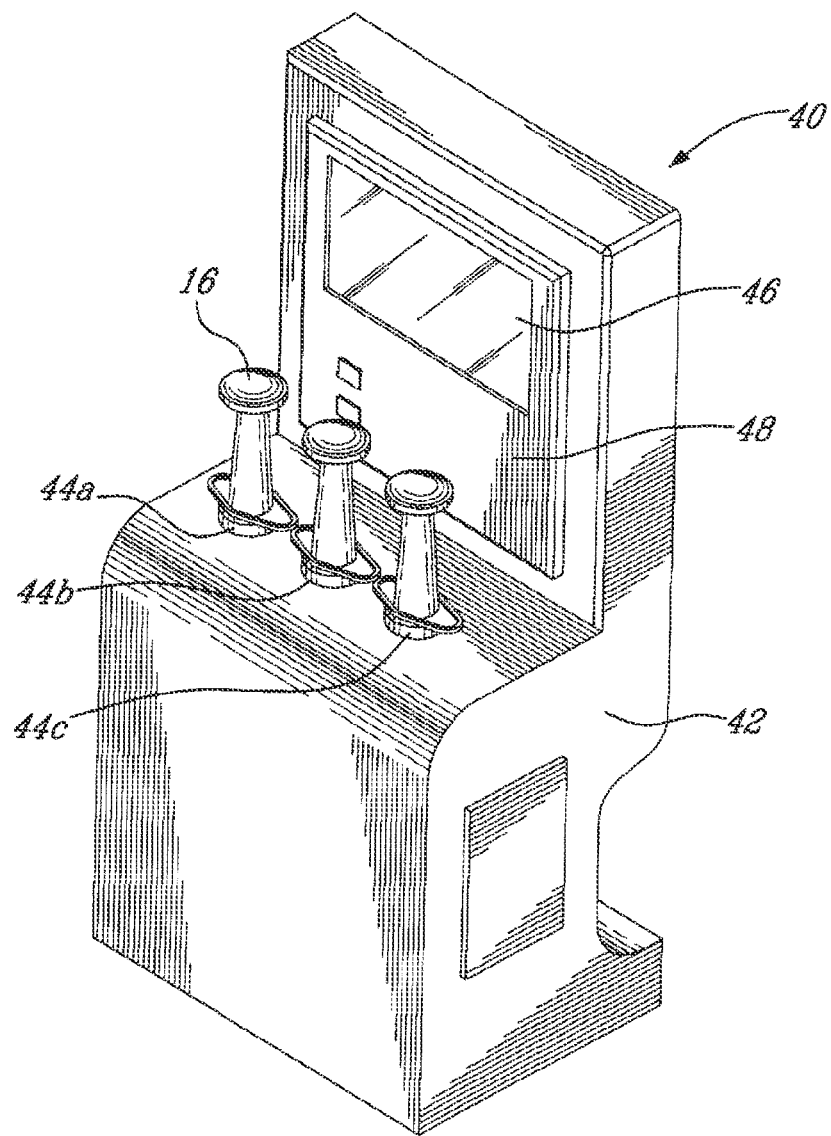

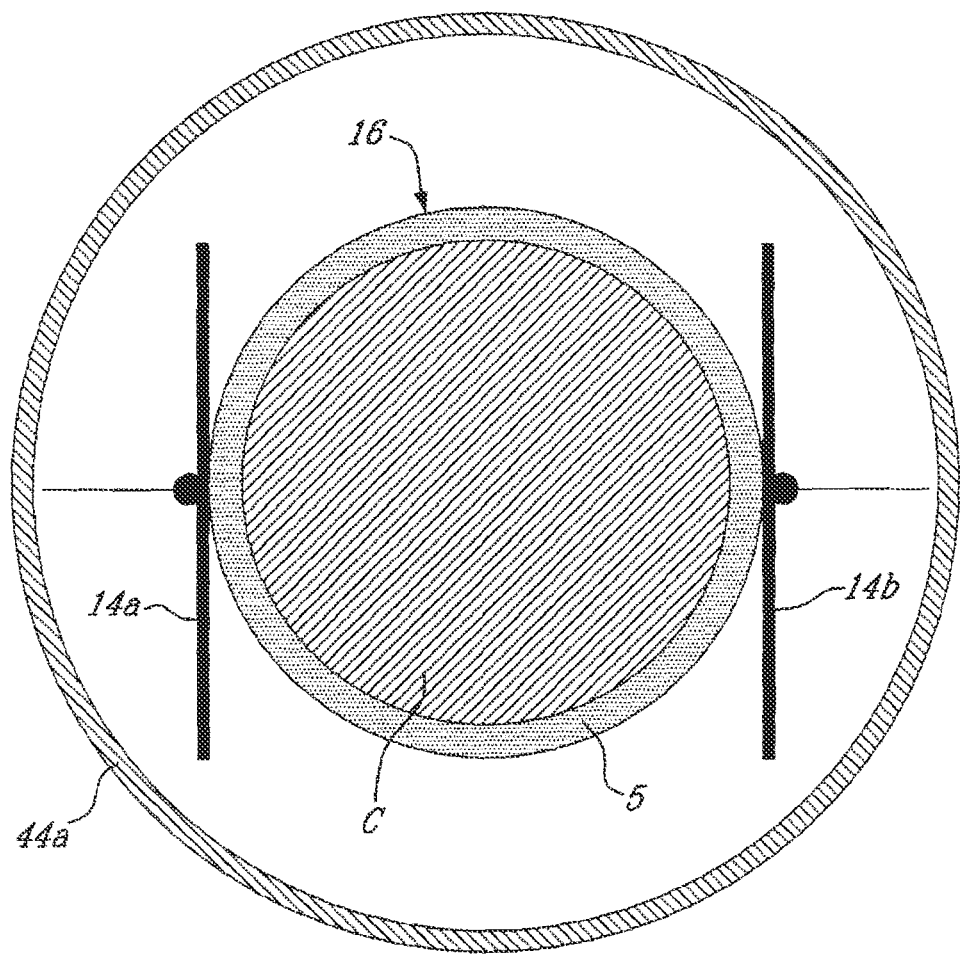

METHOD AND APPARATUS FOR MONITORING AND/OR CONTROLLING THE CURING OF CEMENTS USED IN MEDICAL PROCEDURES

CROSS-REFERENCE OF RELATED APPLICATIONS

The present application is a divisional of U.S. application Ser. No. 12/570,515 filed on Sep. 30, 2009, which is a continuation of PCT application No. PCT/CA2008/000589 filed on Mar. 31, 2008 which claims priority on U.S. Provisional Patent Application No. 60/907,381 filed on Mar. 30, 2007, the entire contents of which is incorporated herein by reference.

FIELD OF THE INVENTION

The present invention relates to a system for monitoring the curing phase of cements, more particularly to monitoring self-curing medical cements that undergo polymerization during curing such as most bone and dental cements as well as means for controlling the time from the mixing of the cement to the initiation of the polymerization as well as the working period after the polymerization has been initiated.

BACKGROUND ART

Acrylic cements are commonly used as bone cements in orthopedic applications, such as joint arthroplasty, in reconstruction procedures, as well as in minimally invasive applications such as for Bone augmentation.

Risks related to bone cement injection procedures result mainly from the open delivery of cement within the bone cavities. The most serious complications can involve cement particles entering the blood stream or the vertebral canals, or emboli caused by the displaced bone marrow, which can be lethal. As such, cement quality is a key determinant for the success of such treatments. Another limitation relates to excess pressure during the delivery through thin long needle for vertebral body augmentation. Excess pressure may cause the destruction of the delivery system or render the physician unable to deliver sufficient cement, resulting in a premature termination of the delivery process. On the other hand physicians may feel the pressure to complete the injection and due to the high pressure combined with the unpredictable curing behavior of the cement may resort to higher delivery rate, which may result in a higher filling rate. The higher filling rate shortens the window of time wherein the cement is delivered and may result in leakage in the due time. Further, excess pressure increases the risk of the monomer being expelled at a higher rate due to a filtration process. This phenomenon is known as filter-pressing and excess monomer has been reported to lead to allergic reaction and potentially the collapse of cardiovascular system functions.

Bone cements are usually formed by dispersing PMMA particles in a monomer. Once the particles and monomer are mixed together, the particles partially dissolve in the monomer and form an increasingly thick cohesive dough. This phase is often known as swelling. This phase is followed by a second phase: the polymerization of the cement, where the thick dough becomes a hard polymeric material.

Because of the aggressive chemical reaction involved in the polymerization and the dependency of both the swelling and the polymerization on specific environmental conditions such as temperature, humidity and method of mixing, the setting process and the properties of the cement used during the operation are generally highly unpredictable and poorly predictable through time, despite the widespread use of polymeric cement in orthopedic applications.

Physicians generally recognize this procedural limitation and have established subjective methods, depending on their experience and preferences, to find the appropriate time for cement delivery and to attempt to improve the outcome of the intervention. In practice, physicians often use visual measures to decide if the cement is ready for application, often describing the right consistency for delivery using terms such as yogurt-like, paste-like, toothpaste-like, dough-like, very dough-like, thick and cohesive, a moderately viscous solution, cake glaze-like or viscous. However, such qualifications are subjective and perceptual.

In the chemical industry, large-scale equipment such as calorimeters and rheometers are used to monitor the setting/solidification process of resins. Though some physicians have started using similar equipment in the operating room, these aparatii are usually large, expensive and require additional personnel and training to operate them.

Furthermore the waiting time prior to the polymerization phase is often considered too long, eight to nine minutes after mixing, for physicians who are under constraints to complete the procedure as efficiently as possible. This waiting time may cause some physicians to prematurely inject the cement into the patient increasing the risk of leakage of the monomer. On the other hand if several interventions are planned it may be desirable to delay the period between the mixing and the polymerization of some batches of the cement. Once the cement reaches adequate thickness, and the ideal application of the cement commences, physicians may desire to increase the effective working time of the doughy cement, in particular when a multilevel-injection is planned. Increasing the effective working time relieves the pressure on the physician, during the injection, and allows the physician to shift focus on the patient's safety instead of being preoccupied with the cement and the ability to deliver it. The ideal cement thickness is reached when the cement fills uniformly and doesn't require excessive pressure to be applied. An added measure of safety of the ideal cement arises from the monomer being consumed by the swelling process and does not filter-press under pressure.

Further, it desirable that the cement behavior becomes predicable and its application is reproducible and consistent.

SUMMARY OF INVENTION

It is therefore an aim of the present invention to provide an improved method of monitoring the polymerization of cement.

It is also an aim of the present invention to provide an improved and objective monitoring system for monitoring the polymerization of cement.

It is a further aim to provide, as an option, a method of controlling the waiting time between mixing and polymerization of the cement.

It is a further aim to provide a method of monitoring and controlling the working time of the cement once polymerization has been initiated.

Therefore, in accordance with one aspect of the present invention, there is provided a method of monitoring a physical parameter of the cement, after mixing, by passing an electric signal through the cement and detecting an initiation point of a polymerization of the cement as indicated by an abrupt change in the electric signal.

Still, in accordance of this invention, the method may be used to monitor both the swelling process and the subsequent polymerization processes. The transition is characterized by the abrupt changes in the electric signal.

In a more specific embodiment of the present invention the method includes passing the electrical signal through a portion of the mixed cement and detecting the change in capacitance, resistivity or phase shift of the electric signal and displaying this data providing the initiation point of the polymerization.

The method of the present invention is of significant utility with medical cement.

Also in accordance with the present invention, there is provided a system for controlling the time period between the mixing and the polymerization of the cement. The use of an ultrasonic signal passed through the mixed cement may cause a reduced time period between the mixing and the initiation point.

Alternatively the cement may be heated to reduce the time period between the mixing and the initiation point.

In another aspect of the present invention the system may comprise a housing defining at least two chambers each adapted to contain a vessel having bone cement therein, the chambers being maintained at different cooling temperatures, and a sensor within each chamber for monitoring a physical parameter of the bone cement, the physical parameter being indicative of a polymerization level of the bone cement, and a display unit displaying data from each sensor. The cooling of the cement may prolong the period before polymerization but is especially useful to prolong the effective working period of the cement after the initiation point.

One of the advantages of properly monitoring and also controlling the initiation point is that the cement is cohesive after the initiation of the cross linking of the molecules and in the case of bone cement the application of such a cohesive cement will result in the expectation that the cement will fill more uniformly.

Once the bone cement attains this cohesion, the viscosity of the cement becomes predictable and therefore, the injection forces required for the delivery becomes predictable and consistent. When using different bone cement batches, monitoring the cement to determine when the cement reaches the inflection point, provides predictability as to when the cement becomes consistent and the forces required for filling are then consistent for each batch. Therefore, unlike existing methods, the forces required to deliver the cement are moderate and the cement delivery does not put high stresses on the pressure applicators or delivery system.

Another advantage is that the monomer is now stable and has already been consummated to make the cement cohesive and therefore, it does not "filter-press" or segregate, when pressure is applied on the cement for injection.

Thus there will be minimum monomer liberated when injecting the bone cement inside the vertebra and therefore, the risk of allergic reaction or cardiovascular pressure collapse is reduced.

Another advantage of the present method of monitoring the polymerization of freshly mixed cement is that the inflection or initiation point can be predicted by interpreting the data during the swelling phase.

BRIEF DESCRIPTION OF THE DRAWINGS

Reference will now be made to the accompanying drawings, showing by way of illustration a particular embodiment of the present invention and in which:

FIG. 3A to 3C are schematic illustrations of a detail of FIG. 1;

FIG. 4 is a perspective view of a syringe including a polymerization sensor according to a particular embodiment of the present invention;

FIG. 5 shows side and bottom view of a plunger of a syringe including a polymerization sensor according to an alternate embodiment of the present invention;

FIGS. 6A, 6B, 6C are graphical representations of the capacitance detected as a function of time from cement mixing, obtained during experiments at different frequencies;

FIG. 7 is a graphical representation of the phase shift of the signal showing seven different frequencies as a function of time from the initiation point, according to a particular embodiment of the present invention;

FIG. 12 is a perspective view of a system for controlling and monitoring the polymerization according to another embodiment of the present invention.

FIG. 13 is a schematic view in cross section of a detail of FIG. 12.

DETAILED DESCRIPTION OF PARTICULAR EMBODIMENTS

Figure 1:
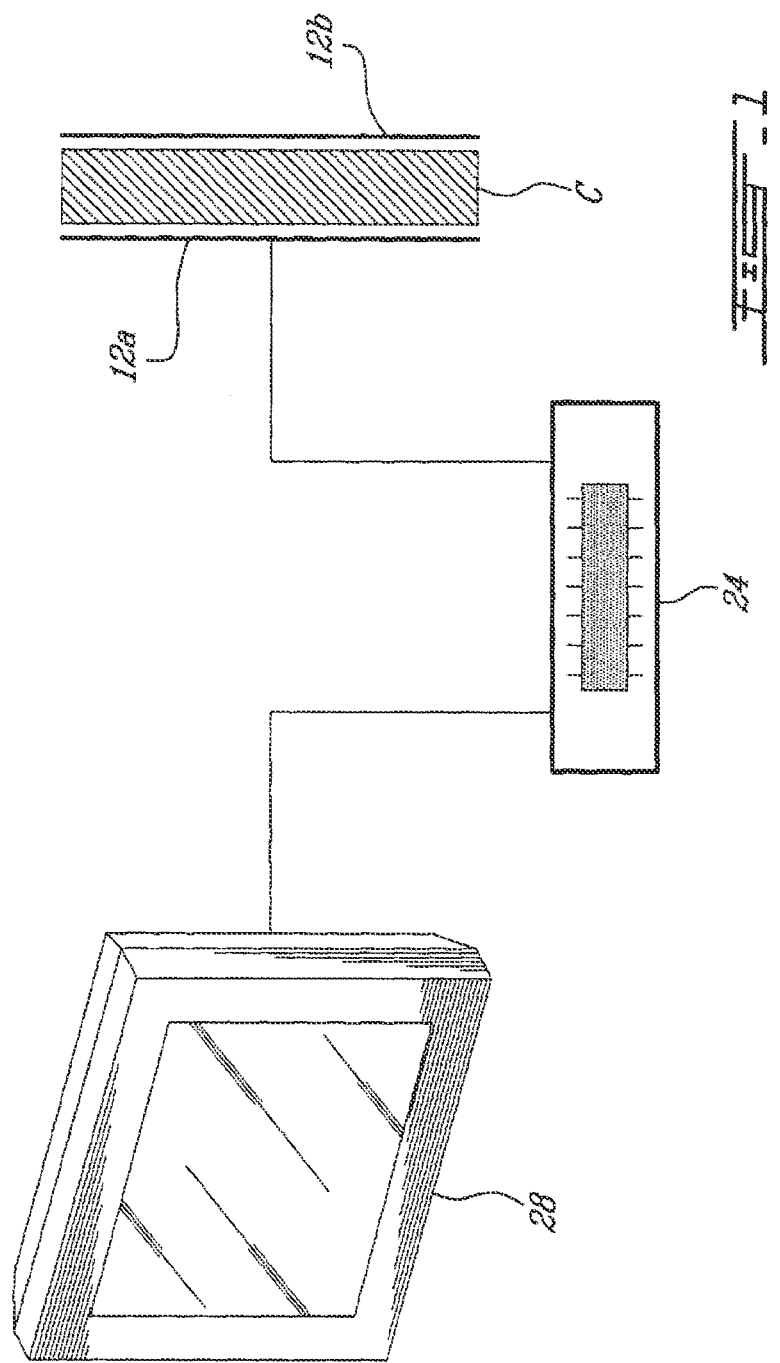
FIG. 1 is a schematic view of the monitoring system according to the present invention.

The proposed system provides a miniature instrumentation allowing the physician to follow and monitor both the swelling and the polymerization of the cement in the operating room in a simple yet efficient fashion that is also non-intrusive and cost effective. Further, the monitoring is done in-situ and requires almost no training or extra equipment.

In one embodiment as shown schematically in FIGS. 1 to 3C a cement sample C is placed in a vessel 5 and dielectric sensors or electrodes 12a and 12b are placed on opposite sides of the cement sample C. The dielectric electrodes 12a, b are connected electrically to an electronic circuit board 24 which is programmed to track the capacitance/resistivity of the chemical reaction occurring in the freshly mixed cement C. The circuit board 24 is connected to a display screen 28 in order to display the results.

FIGS. 3A, 3B and 3C illustrate schematically different electrode configurations. In FIG. 3A the electrodes 12a, b are in contact with the cement C while in FIG. 3B the electrodes are on the exterior of a vessel 5 containing the cement C. FIG. 3C illustrates a circular or tubular vessel 5 with plate like electrodes 12a, b.

Referring to FIG. 4, a syringe 16 which can be part of a bone cement delivery device is equipped with a polymerization sensor such as an electrode according to a particular embodiment of the present invention. The polymerization sensor is a dielectric sensor, which measures the capacitive and conductive properties of the bone cement during setting. The sensor includes two thin plates 14a placed around the syringe body 16 containing the bone cement. The plates 14a are made of an electro-conductive material and together define a capacitor. As the cement swells and polymerizes, the capacitive properties of the cement change, and this change is detected by the capacitor because of the changing dielectric properties of the bone cement.

In the embodiment shown, the dielectric sensor formed by plates 14a is a contact-less sensor, as the plates are placed on an outer surface 18 of the syringe body 16, i.e. not in contact with the bone cement. The plates 14a are curved and define a holder, similar to a battery charger, which retains the syringe body 16 between the plates 14a, for example through the action of springs 20. Alternately, the plates 14a can be permanently attached to the outer surface 18 of the syringe body 16.

In an alternate embodiment, the plates 14a are defined by a thin metallic layer forming an electro-conductive film and deposited on the outer surface 18 of the syringe body 16 using an adequate process such as, for example, electro-less liquid coating or metal vapor deposition. The functional thickness of the thin metallic layer is preferably a few microns.

In an alternate embodiment, the dielectric sensor is a contact sensor, and the plates 14a, which can be in the form of an electro-conductive film as described above, are placed inside the syringe body 16 and in contact with the bone cement, for example on the syringe plunger (similar to the embodiment of FIG. 5 which will be described further below) or on an inner surface of the syringe body 16.

In another alternate embodiment similar to FIG. 3C, the sensor includes two parallel electro-conductive plates and the syringe 16 containing the bone cement is placed there between. An alternating or direct voltage is applied to the plates, generating a bulk electrical field across the cement to obtain readings of the electrical properties of the cement. An advantage of this embodiment is that is it simple and the electrical field is uniform.

Referring to FIG. 5, a polymerization sensor according to another embodiment of the present invention is shown. The polymerization sensor is an electro-resistive sensor, and includes two electro-conductive plates or elements 14b which are in contact with the bone cement and which each define an electrode. A direct electrical current is then sent from one electrode to the other across the cement. As the cement polymerizes its resistive property changes, the change in the electric properties being indicative of the setting of the cement.

In the embodiment of FIG. 5, interdigitating electrodes are used, enhancing the efficiency of the sensor, each interdigitating electrode resembles a comb with sufficient spacing between individual fingers to accommodate the fingers of the complementary electrode. An alternating voltage is applied to the interdigitating electrodes which produce an electric field extending into the cement. The electrical current is proportional to the attenuation or the electro-conductive cement properties. The polymerization of the cement leads to a reduction of the electrical current due to the increase in the electric resistance of the hardening cement and thus the change in decline in current provides a reading of the cement setting.

Rather than monitoring changes in the capacitance or resistivity of the cement in a syringe during the procedure, an alternative would be to provide a mirror sample, when the cement is mixed and to monitor the mirror sample rather than the cement in the syringe. A small vessel or container 5, such as is shown schematically in FIGS. 3B and C, is provided that is capable of receiving a small mirror sample of 5 cc or greater of the freshly mixed cement. The electrodes 12a, b provided on the outer surface of the vessel 5 would then provide and detect the electrical signal passing through the cement C. The changes in the cement C would be similar to that occurring in the syringe ready to be injected to the patient.

Figure 2:
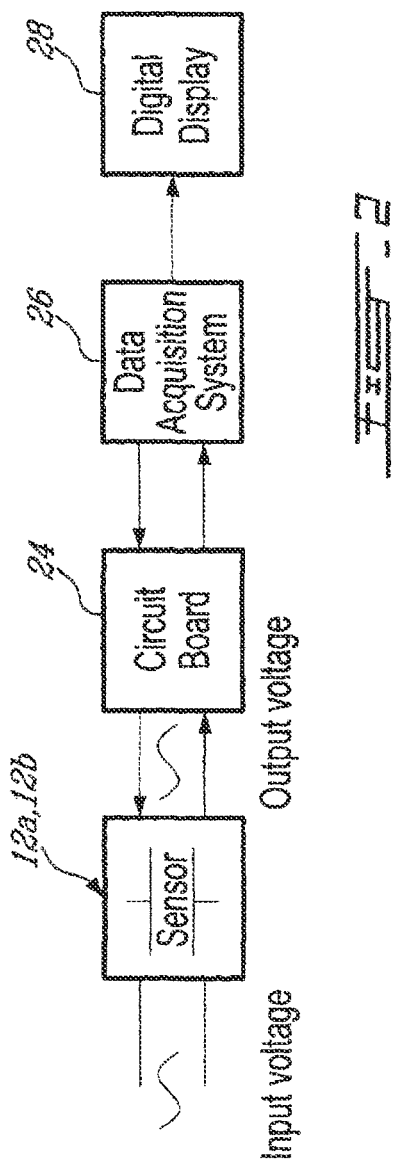
FIG. 2 is a block diagram of a polymerization monitoring system according to a particular embodiment of the present invention.

Referring to FIG. 2, a monitoring system according to the above embodiments of the present invention is shown, which is used for example with the electrodes 12a, b described above. The monitoring system includes a controller, for example in the form of an electrical circuit board 24, which controls an electrical alternating or non alternating signal sent across the plates or electrodes 12a,b which, while crossing the cement C, undergoes some attenuation and shift. The electrodes 12a, b measures the electrical properties of the cement C and sends a corresponding signal to the circuit board 24.

The circuit board 24 reads and potentially amplifies the output signal from the electrodes 12a,b, and sends the potentially amplified data from the electrodes 12a,b to a data acquisition system 26, which transfers the received analog signal into a digital signal. The data acquisition system 26 sends the digital signal to a digital display unit 28. The digital display unit 28 thus displays the dielectric properties of the bone cement C as read by the electrodes 12a, b.

Advantageously, the monitoring method described herein uses an inflection point describing the initiation of cement polymerization. This inflection point is followed by the formation of cross-linked polymer and is characterized by the rapid change in cement properties. The significance of this inflection point is that the monitoring method is predictive instead of being only detective of the cement curing property.

Of particular importance is the initiation of the polymerization process of the bone cement, which occurs through free radicals. Accordingly, the polymerization is called radical polymerization. This polymerization process, once initiated, leads to a large number of radicals in the cement, often called free radicals. These radicals are electrically charged particles and have a large impact on the dielectric properties of the cement because they change the electro-conductivities of the cement significantly.

The sensor can detect this radical change in the dielectric properties of the cement and, accordingly, the initiation of the cement polymerization.

Some polymeric cement may not show an inflection point. However, the monitoring system can still detect a transition from the swelling to the polymerization phase.

Additives such as Barium sulphate used to enhance the opacity of the cement under fluoroscopy may cause a change in the indicative signal or delay the polymerization process. Still, the system is able to monitor the swelling and the polymerization process and detect the transition in order to display the initiation of polymerization.

Although the polymerization sensors or electrodes 12a,b; 14a, b have been described as dielectric or electro-resistive sensors, in alternate embodiments, the polymerization sensors include any one of piezoelectric sensors, a conductive grid, photonic sensors, reflective sensors and spectroscopic sensors, all measuring properties of the cement indicative of its setting.

Additional details on the polymerization sensors can be found in the PCT published application WO2007/115402 A1 entitled "CEMENT DELIVERY SYSTEM FOR BONE AUGMENTATION PROCEDURES AND METHOD" which is incorporated herein by reference in its entirety.

Initiation Point Detection Experiments

Over 200 experiments have been conducted with an instrumented syringe 16 such as shown in FIG. 4, including dielectric sensors 14a. Once the vessel 5 or syringe 16 has been filled with PMMA cement, the electrical signal attenuation and phase shift as measured by the sensors 14a was examined.

Figure 6A:
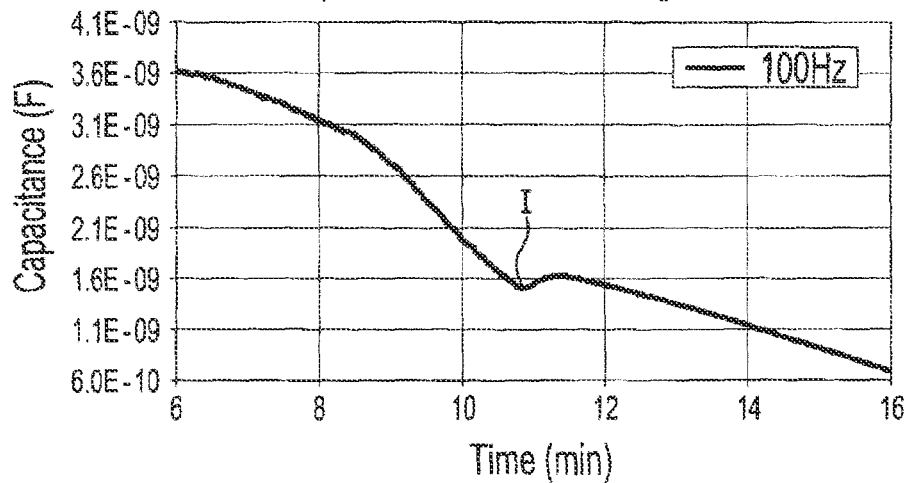

Referring now to FIGS. 6A to 7 it can be seen that the attenuation of the signal is remarkable and is strongly correlated with the phase shift with respect to time. The signal shows a first feature representative of the swelling process, and a second feature representative of the fast changes and polymerization of the cement. The transition between the swelling and polymerization is characterized by an inflection point denoting the initiation process or the initiation point I where suddenly a large population of radicals become available. Because of the large birth rate of these radicals/dipoles that are electrically charged, there is a significant and sudden change in the electrical signal obtained in the capacitor.

These results support the hypothesis that the initiation point in time is visible because of its abrupt nature.

The initiation point I is predictive of subsequent cross-linking of polymer network and rapid changes in cement behavior and finally curing. The establishment of this initiation point I is really a monitor for the setting process of the cement.

The tests revealed that the time of the initiation point may vary over a few minutes. However the initiation point represents a process-related predictor, which improves the predictability of the results and brings consistency in the application of the cement. In addition, the dielectric signal shows the progress of the swelling process and the subsequent polymerization process. In fact the inflection point may be predicted by reading the curve showing the swelling process.

In the following experiments, the signal frequency was varied in order to determine the preferred range of frequencies to best detect the inflection or initiation point.

Figure 6B:
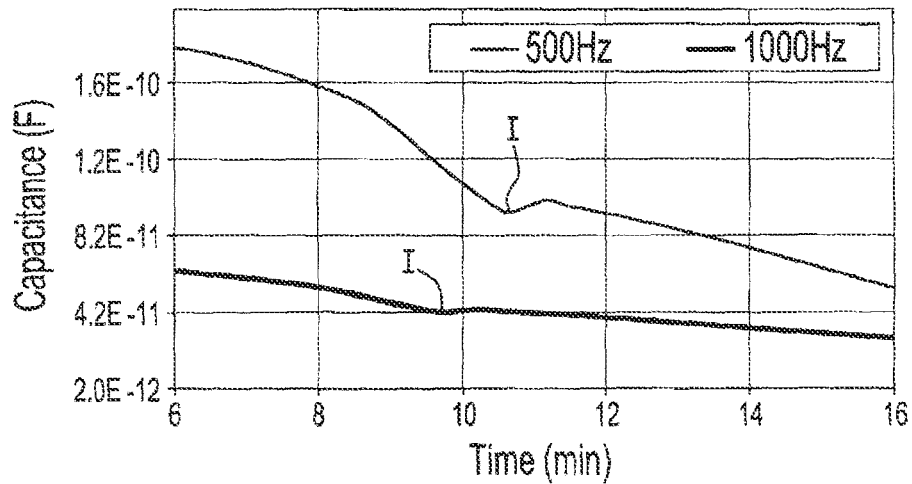

| Experiment | Frequency | Humidity | Temperature |
| --- | --- | --- | --- |
| 1. FIG. 6A & FIG. 7 | 100 Hz | 17% | 20.9° C. |
| 2. FIG. 6B & FIG. 7 | 500 Hz | 17% | 21° C. |
| 3. FIG. 6B & FIG. 7 | 1000 Hz | 17% | 21.1° C. |
| 4. FIG. 6C & FIG. 7 | 5000 Hz | 17% | 21.1° C. |
| 5. FIG. 6C & FIG. 7 | 10000 Hz | 17% | 21.3° C. |
| 6. FIG. 6C & FIG. 7 | 20000 Hz | 17% | 21.1° C. |
| 7. FIG. 6C & FIG. 7 | 100000 Hz | 14% | 21.3° C. |

As can be seen the lower frequencies are better suited for detecting the abrupt changes in phase shift or capacitance change. The preferred range is between 100 Hz and 20 kHz.

Ultrasonic Treatment of Cement

With the use of an ultrasonic system, the waiting time can be reduced significantly. Ultrasonic waves will compress and expand in the cement when travelling through it. The energy of the ultrasound wave creates cavitations, which involves the formation, growth and impulsive collapse of the cavitations in the form of micro-bubbles in the cement. Specifically, these bubbles are generated by negative pressure during the rarefaction phase of the sound wave if sufficiently large to disrupt the liquid. This is particularly applicable to the cement before attaining the inflection point.

An embodiment including the ultrasonic system will be described later in relation to FIG. 14.

Injection Experiments

The following experiments provide a deeper understanding to how this process-related initiation point makes cement behavior more predictable, as compared for example to using the time since cement mixing as a reference. It is illustrated by measuring the injection forces that are required to deliver PMMA cement through a thin and long cannula. In these experiments, the forces required for delivery were measured, representing the forces the physician would encounter when pushing the plunger of the syringe. These experiments essentially mimicked the clinical conditions of bone cement injection.

These experiments have been conducted over several days to ensure the validity of the results. The experiments were conducted according to the following:

1) The cement powder and monomer are weighed according to the ratio recommended by the manufacturer.

2) A first stopwatch is started as soon as the cement powder is mixed with the monomer.

3) The mixture is manually mixed for 20 seconds and then placed in an oscillator at 30 seconds at a speed of 400 Hz for an interval of 90 seconds.

4) The ambient temperature and humidity are recorded.

5) A first syringe, used for the injection, is then filled and plugged with a cap.

6) The remaining cement is then immediately poured into a second syringe and placed in functional relationship with a dielectric polymerization sensor such as 12a described above. The electrical monitoring of the cement within the second syringe is started.

7) The first syringe is then placed in a Materials Testing machine.

8) The flow rate of the machine is set to 1.6 ml/min.

9) The electrical data (phase shift and attenuation) of the cement within the second mirror syringe is carefully monitored until the initiation point is reached. This initiation point I appears on a graph as a sudden increase in the electrical data causing the curve to go back up for a few seconds before continuing its downward slope.

10) Once the initiation point is reached, a second stopwatch is started to measure a 30 seconds delay until the injection with the first syringe is started.

11) Approximately 10 seconds after the initiation point is reached, the cap is removed from the first syringe and the cannula is screwed on; at exactly 30 seconds after the initiation point is reached (or, in the case of the first day, at roughly 30 seconds after the initiation point is reached), the injection with the first syringe starts and the force necessary for the injection is measured.

12) The injection proceeds for approximately 3 minutes or as long as it takes to inject the full amount of cement within the first syringe.

13) The electrical monitoring of the second syringe continues until the cement fully polymerizes, which is shown on the curve by the data becoming constant at the bottom of the slope.

The results of 19 injection experiments conducted over four different days under realistic variable environmental conditions are shown in FIGS. 8A to 11B.

Figure 8A:
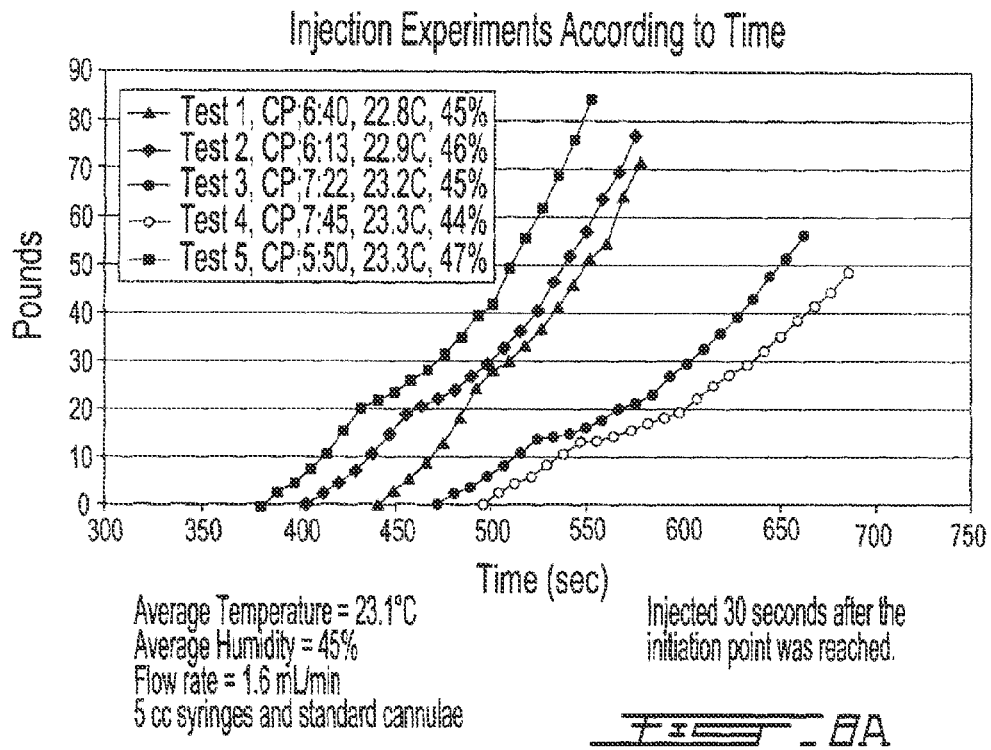
FIG. 8A is a graphical representation of bone cement injection forces as a function of time from cement mixing, obtained during a first day of experiments.
Figure 8B:
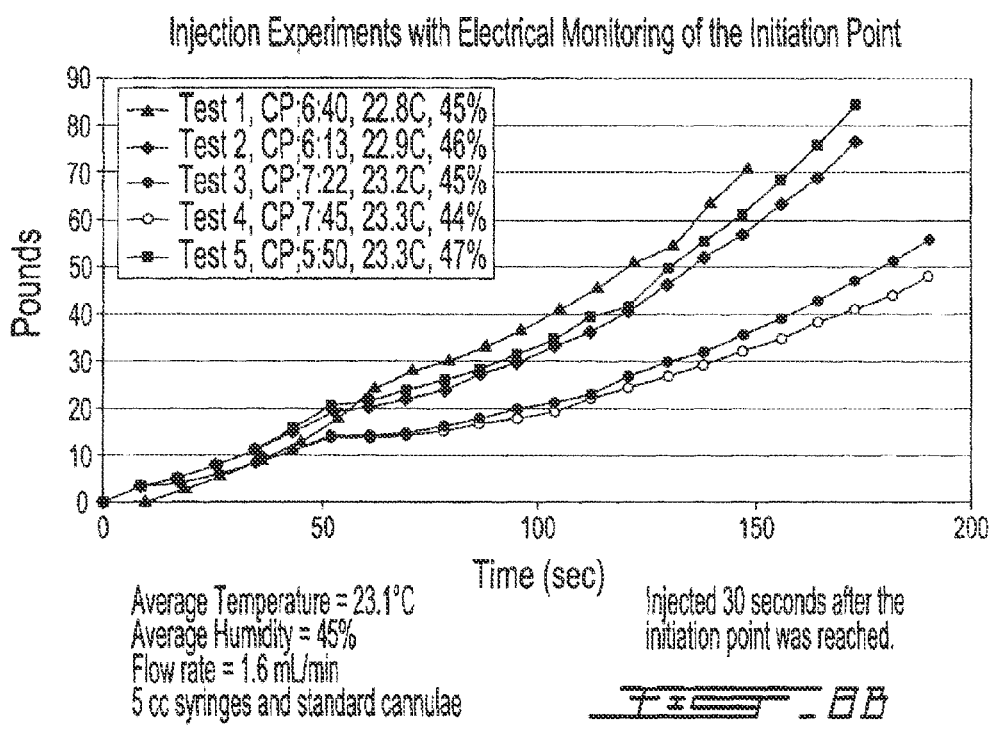
FIG. 8B is a graphical representation of the injection forces of FIG. 8A as a function of time from the initiation point, according to a particular embodiment of the present invention.

FIGS. 8A-8B show the results obtained in five experiments performed on a first day. FIG. 8A shows the injection forces displayed with respect to the time from cement mixing, while FIG. 8B shows the same injection forces with respect to the time from the end of the 30-second interval following the initiation point, i.e. t=0 represents the end of that 30 second interval. It is to be noted that for these experiments the 30-second interval was computed with a stopwatch but less precisely than for the following experiments).

It can be seen from a comparison of FIGS. 8A and 8B that the data between the different experiments is substantially more consistent when using the initiation point as a time reference.

Figure 9A:
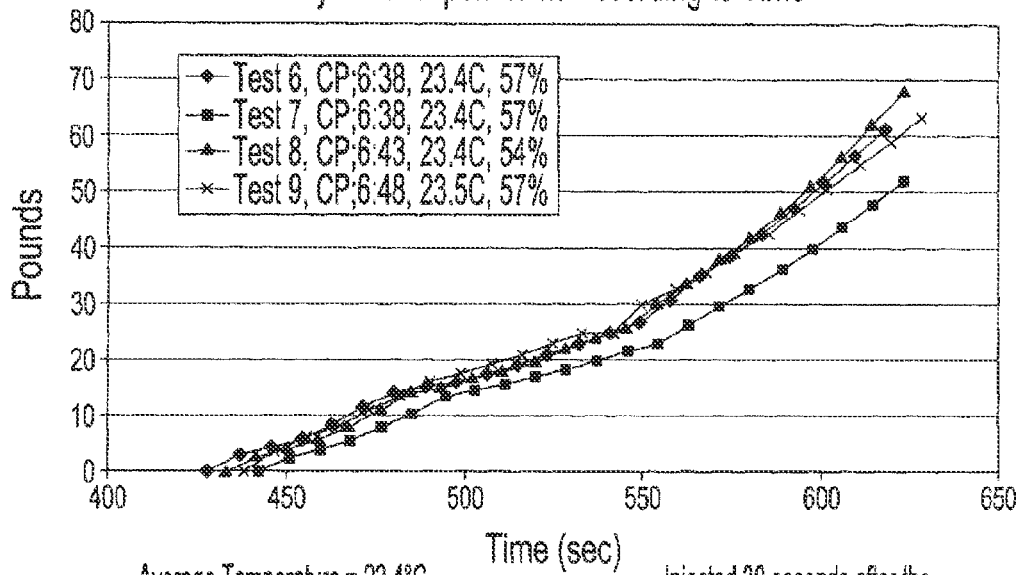
FIG. 9A is a graphical representation of bone cement injection forces as a function of time from cement mixing, obtained during a second day of experiments.
Figure 9B:
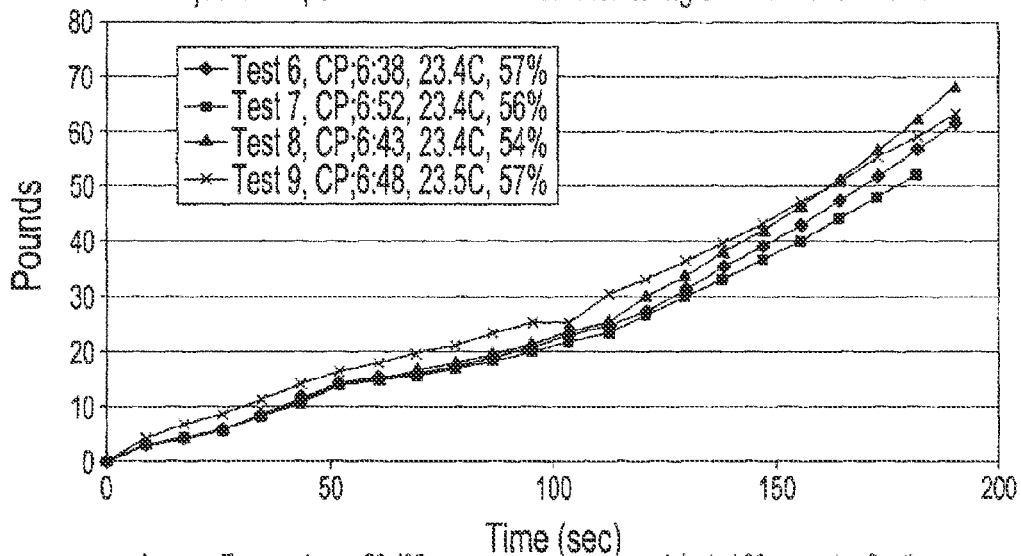
FIG. 9B is a graphical representation of the injection forces of FIG. 9A as a function of time from the initiation point, according to a particular embodiment of the present invention.

FIGS. 9A-9B show the results obtained in four experiments performed on a second day, with FIG. 9A depicting the injection forces as a function of time since the cement mixing, and FIG. 9B depicting the injection forces as a function of time since the end of the 30 second interval after the initiation point. The data with respect to the time since the initiation point is again more consistent than the same data with respect to the time since the mixing.

Figure 10A:
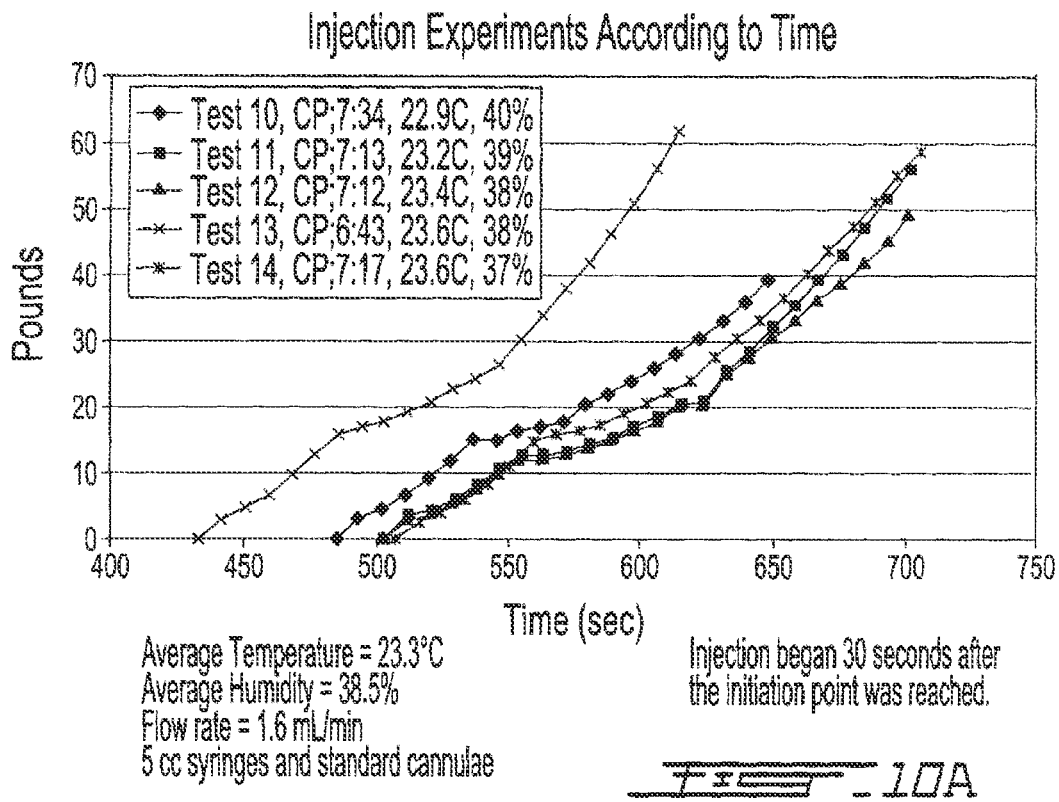
FIGS. 10A is a graphical representation of bone cement injection forces as a function of time from cement mixing, obtained during a third day of experiments.
Figure 10B:
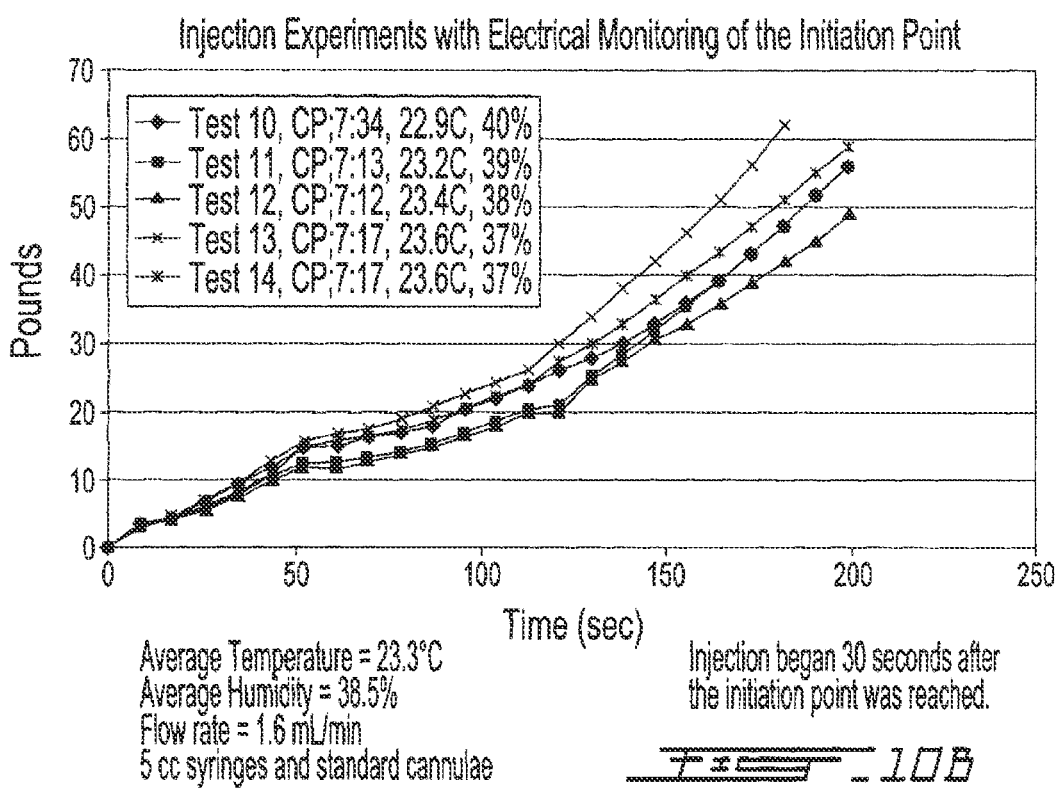
FIG. 10B is a graphical representation of the injection forces of FIG. 10A as a function of time from the initiation point, according to a particular embodiment of the present invention.

FIGS. 10A-10B show the results obtained in five experiments performed on a third day, again with FIG. 10A depicting the injection forces as a function of time since the cement mixing, and FIG. 10B depicting the injection forces as a function of time since the end of the 30 second interval after the initiation point. Again, a higher degree of consistency of the results can be observed with respect to the results represented as a function of time since the initiation point.

Figure 11A:
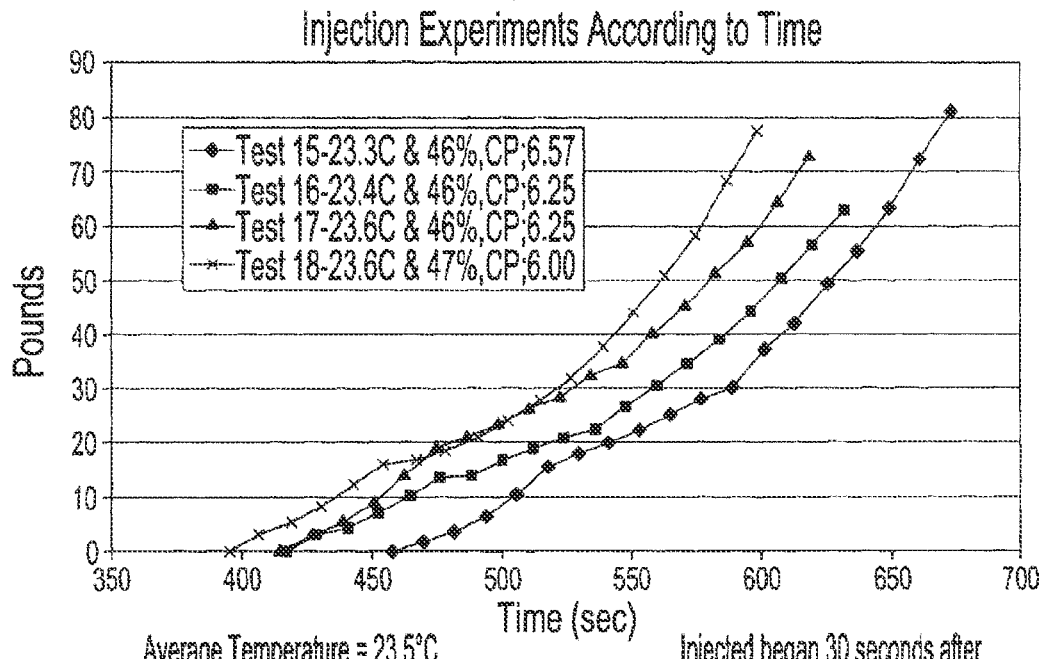
FIG. 11A is a graphical representation of bone cement injection forces as a function of time from cement mixing, obtained during a fourth day of experiments.
Figure 11B:
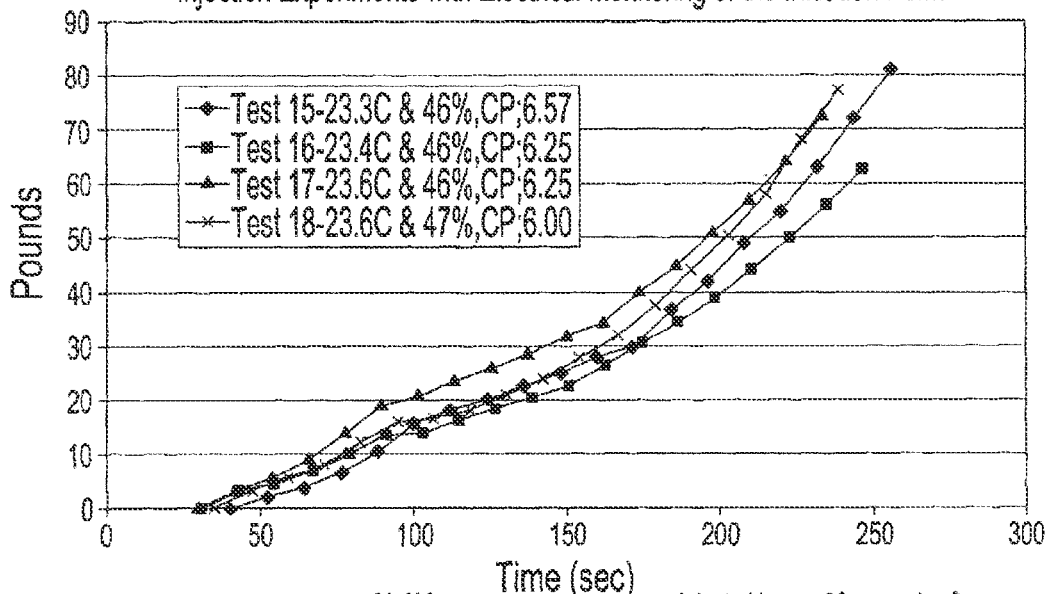
FIG. 11B is a graphical representation of the injection forces of FIG. 11A as a function of time from the initiation point, according to a particular embodiment of the present invention.

FIGS. 11A-11B show the results obtained in four experiments performed on a fourth day, again with FIG. 11A depicting the injection forces as a function of time since the cement mixing, and FIG. 11B depicting the injection forces as a function of time since the end of the 30 second interval after the initiation point. The significant difference observed in the consistency of the two Figures further verifies the trend seen on the previous days.

The results thus show that the use of the initiation point as a reference leads to an improved reproducibility of the injection force results, which depends on the viscosity/viscoelastic behavior of the cement. As such, the use of the initiation point as a reference allows for good predictability of the consistency of the cement and therefore of the injection and filling behavior.

The polymerization sensors allow for the monitoring and determination of the initiation point, which can then be used to indicate when injection should be started (e.g. 30 seconds after the detection of the initiation point). Such a monitoring method is effective and relatively easy to implement. It is an inexpensive solution that provides a significant enhancement in increasing the predictability when working with bone cement.

In a particular embodiment of the invention, the injection of the cement is thus guided by the determination of the initiation point; the injection beginning a given period of time after the initiation point is detected.

Leakage experiments conducted according to the protocol established by Baroud et al. (2006), Volume 31, Number 22, pp 2562-2568 showed that a cement injected 45 seconds post initiation point does not leak and fills more uniformly in the substitute model.

In a particular embodiment as shown in FIGS. 1 and 2, a monitoring system is provided and includes a display unit 28 connected to the polymerization sensors 12a, b and displaying the information provided thereby. Through experimentation, for example similarly to the experiments described above, a typical injectability time after the initiation point is determined for specific cement. The predictability of the results when examined as a function of time from the initiation point allows for such a typical injectability time to be determined in a substantially accurate manner, which would not be the case with the results being examined as a function of time from the cement mixing, for example. This typical injectability time is programmed in the monitoring system, which can then inform the physician of an approximate time left for the injection of the cement once the initiation point is reached. As such, the physician can more easily plan the bone cement injection procedure(s) being performed with the particular batch of cement being monitored.

The polymerization sensors 12a, b and 14a, b thus enhance the predictability of the cement behavior, providing an objective parameter as an injection reference and eliminating the need for subjective determination of whether the cement is ready or not for injection.

The sensors can be easily integrated in existing cement delivery devices, and as such the method of using the initiation point as a reference for injection can be easily implemented in a clinical practice.

The system can be provided as a stand alone system to be used in any application of self-curing cements. By supplying a mirror sample vessel provided with a sensors and a detecting circuit combined to a monitor, the polymerizing phase of the cement can be monitored and an exact initiation point can be determined allowing more precise and predictable applications of the cement.

Although the experiments have been conducted with bone cement to be used in vertebroplasty similar use of the system can be advantageously applied to other orthopedic procedures and even dental cement applications.

The sensors and method can be used in vertebroplasty but also in any other bone cement injection application where PMMA cements are used.

Although the method was tested using PMMA cement, it is anticipated that the same or a similar method could be applied to other types of bone cement such as, for example, calcium phosphate.

Similarly, although the initiation point was determined using dielectric sensors, it is anticipated that a similar initiation point can be determined using other types of sensors such as those listed above.

Embodiment with Cooling System

Referring to FIGS. 12 and 13, a monitoring system 40 according to another embodiment of the present invention is shown. The monitoring system 40 comprises polymerization sensors such as 14a, b described in the previous embodiments or any other adequate sensor, and additionally comprises a cooling system for delaying the polymerization of the cement.

By cooling the cement at different temperatures, different syringes 16 containing cement prepared at the same time from the same cement batch can be ready for injection at different points in time. Such a cooling system is useful when a physician wants to perform successive bone cement injections, for example in a multilevel vertebroplasty. Often, when such successive bone cement injections are performed, the preparation of a new cement mix can be required between successive injections and/or the time available to the physician for performing the injections is limited by the cement hardening, thus reducing the available time for each injection as the total number of injections increases.

The monitoring system 40 thus provides for different syringes to become ready for injection at different points in time through local cooling of each syringe. The physician controls the cooling level and therefore controls when the cement within each syringe becomes ready for injection.

In the embodiment shown, the monitoring system comprises a body 42 defining three polymerization monitoring chambers 44*a, b, c*, each being sized and designed to receive a syringe 10 therein. In a case where the syringes 16 include integral polymerization sensors 14*a, b*, each monitoring chamber 44*a, b, c* also includes adequate connections for receiving data from the polymerization sensors 14*a, b* of the syringe 16 received therein. In a case where non instrumented syringes 16 are received in the monitoring chambers 44*a,b,c*, each chamber includes polymerization sensors 14*a, b*, disposed to be in functional relationship with the syringe 16 received within the respective chamber.

The monitoring system 40 further comprises a display unit 46 displaying the readings from the polymerization sensors 14*a, b* as well as temperature information for each chamber 44*a, b, c*, and a control panel 48 for accepting commands from the physician.

The three monitoring chambers 44*a, b, c* include a cold chamber 44*a*, a cool chamber 44*b* and a room temperature chamber 44*c*. In a particular embodiment, the cold chamber 44*a* keeps the syringe 16 contained therein at a temperature of −10° C. or even lower, and the cool chamber 44*b* keeps the syringe 10 contained therein at a temperature of 0° C. Other adequate temperatures can be selected, and the body 42 of the monitoring system 40 can alternately define more or less than three chambers. Each syringe 16 is kept within its respective chamber 44*a, b*, and *c* during a predetermined period of time depending on a desired polymerization level. In a particular embodiment the polymerization level is evaluated with respect to time lapsed since the initiation point, as described above.

In use, the syringe contained within the room temperature chamber 44*c* is used first for injection. The syringe from the cool chamber 44*b* is then used, and the syringe from the cold chamber 44*a* is used last. The temperature difference between the chambers 44*a,b,c* allows for the cement within the syringe from the cool chamber 44*b* to be ready for injection after the cement within the syringe from the room temperature chamber 44*c* is ready, and preferably after injection with the syringe from the room temperature chamber 44*c* is finished, and similarly, for the cement within the syringe from the cold chamber 44*a* to be ready for injection after the cement within the syringe from the cool chamber 44*b* is ready, and preferably after injection with the syringe from the cool chamber 44*b* is finished.

In a particular embodiment, the syringes 16 are cooled with elements producing thermoelectric cooling, forming a Peltier cooler. The elements are connected to a temperature regulator which regulates the temperature within the respective chamber. As such, the cooling elements can be an integral part of the syringes 16, for example having a disposition similar to that of the polymerization sensors 14*a, b*, with the temperature regulator being contained within the body 42 and the connections to the temperature regulator being provided in each chamber 44*a, b, c*, or the cooling elements can be separate from the syringes 16 and provided in each monitoring chamber 44*a, b, c*.

In a particular embodiment, the monitoring chambers 44*a, b, c* are sized to each contain a standard 5 ml syringe 16 having polymerization sensors 14*a, b* attached thereto. The polymerization sensors 14*a, b* are connected to the display unit 46 such as to monitor data provided thereby.

Each of the cold and cool monitoring chambers 44*a; b* includes four Peltier elements each mounted on a corner post, the corner posts being mounted on a leak proof base. A syringe 10 containing the bone cement is suspended within each chamber 44*a, b* by a leak proof support located at the top of the chamber 44*a*, and *b*. All elements of the chambers 44*a, b* with the exception of the Peltier elements are preferably made of plastic.

As soon as each syringe 16 is inserted within the respective chamber 44*a, b*, an electrical current is circulated through the Peltier elements in order to cool the syringe 16 to the desired temperature.

The room temperature chamber 44*c* does not contain any cooling elements and receives a syringe 16 which is kept at room temperature for injection. The syringe 16 is similarly retained within the room temperature chamber 44*c* by a leak proof support located at the top of the chamber 44*c*.

The monitoring system 40 thus provides for an increased, injectable period for a cement batch, reducing cement waste when performing multiple procedures and allowing increased time for each procedure, while monitoring the cement to ensure that the cement within each syringe is injected when the appropriate viscosity is reached.

Figure 14:
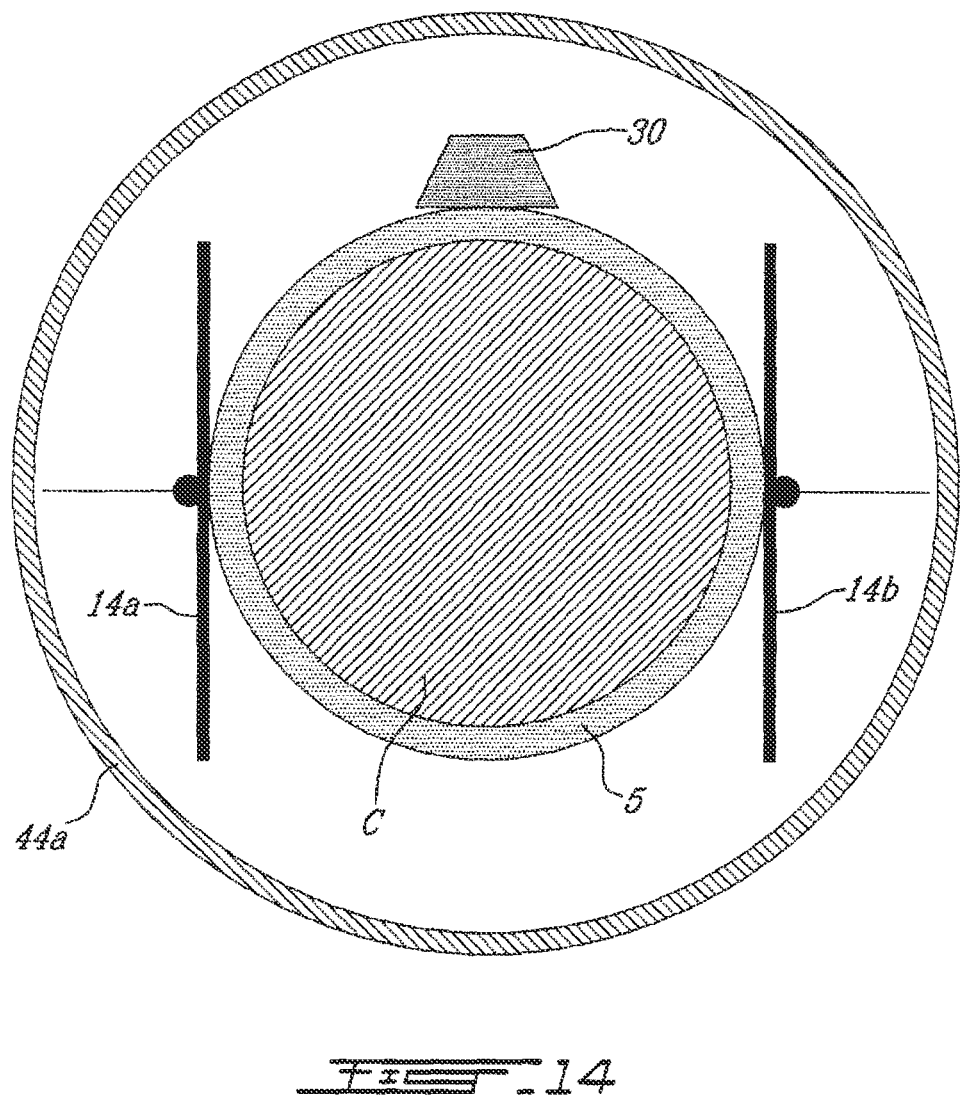
FIG. 14 is a schematic view similar to FIG. 13 showing a further embodiment of the invention.

FIG. 14 shows a similar cooling and monitoring device but integrating an ultrasonic emitter 30. As previously described the ultrasonic emitter 30 may be used to reduce the wait time for the inflection or initiating point from the mixing step. Thus when combined with the Peltier cooler, the device could be used to reduce the waiting time to the initiation point and extend the effective working time to allow the physician more time to accomplish several vertebroplasties.

Alternatively a Peltier device may be used to heat the cement to thereby reduce the time between mixing and the initiation point.

The ultrasonic emitter 30 will be placed around the cement chamber 5. There can be multiple sensors placed. Both longitudinal and transverse ultrasonic waves will be used with a preferred range of frequency from 1 to 5 MHz. Other frequencies can be used. The ultrasonic wave emitter 30 produces a wave which gets dissipated inside the cement and because of the cavitations effect, the swelling of the cement can be accelerate and the initiation point can be reached earlier.

An alternative embodiment would be to utilize the Peltier devices to heat the cement, between the mixing and the initiation point I in order to reduce the swelling phase time. The temperature increase should not exceed 10° C. above room temperature.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. An apparatus for determining an initiation point of cement curing, comprising a vessel for containing at least a portion of freshly mixed cement, means for passing an electric signal through the cement, means for detecting an abrupt change in a dielectric or electric property of the cement as a result of the electric signal and a display unit for displaying the initiation point of polymerization of the cement from the abrupt change in the dielectric or electric property detected, the change in the dielectric or electric property being a phase shift in the electric signal passed through the cement or a change in capacitive properties of the cement or a change in resistivity of the cement.

2. The apparatus as defined in claim 1 including a sensor for passing and reading the electric signal made up of a pair of electrodes adapted to be placed in a spaced apart arrangement whereby the cement is placed between the electrodes and an electronic circuit is electronically connected to the electrodes.

3. The apparatus as defined in claim 1 wherein the vessel is a syringe forming part of a bone cement injection system.

4. The apparatus as defined in claim 2 wherein the vessel is a stand alone cement receiving container mounting the electrodes.

5. The apparatus as defined in claim 2 wherein the electrodes are mounted on outer surfaces of the vessel and out of contact with the cement.

6. The apparatus as defined in claim 2 wherein the electrodes are mounted on the vessel in contact with the cement.

7. The apparatus as defined in claim 1 wherein an ultrasonic emitter is provided for passing an ultrasonic wave through the cement to reduce the time period from the mixing of the cement to the initiation point.

8. An apparatus for determining an initiation point of cement curing, comprising a vessel for receiving the cement, electrodes connected to the vessel and configured to pass an electric signal through the cement, and at least one sensor configured to monitor a dielectric or electric property of the cement as a result of the electric signal and detect an abrupt change therein, and a monitoring system connected to the at least one sensor and configured to display the initiation point of polymerization of the cement from the abrupt change in the dielectric or electric property detected, the change in the dielectric or electric property being a phase shift in the electric signal passed through the cement or a change in capacitive properties of the cement or a change in resistivity of the cement.

9. The apparatus of claim 8, wherein the electrodes are part of the at least one sensor.

10. The apparatus as defined in claim 9 wherein the electrodes are mounted on outer surfaces of the vessel and out of contact with the cement.

11. The apparatus as defined in claim 9 wherein the electrodes are mounted on the vessel in contact with the cement.

12. The apparatus of claim 8, wherein the at least one sensor includes two electro-conductive plates placed around the vessel each defining one of the electrodes and together defining a capacitor.

13. The apparatus as defined in claim 8 wherein the vessel is a syringe forming part of a bone cement injection system.

14. The apparatus as defined in claim 8 wherein an ultrasonic emitter is provided for passing an ultrasonic wave through the cement to reduce the time period from the mixing of the cement to the initiation point.

15. The apparatus as defined in claim 8, wherein the vessel defines at least two chambers each adapted to contain a body having cement therein, the chambers being maintained at a different temperature from one another, the at least one sensor includes a sensor in connection with each chamber.

16. The apparatus as defined in claim 15, wherein at least one of the chambers include cooling elements configured to be in heat exchange relationship with the body having the cement therein.

17. The apparatus as defined in claim 8, wherein the at least one sensor is an electro-resistive sensor including two electro-conductive plates in contact with the bone cement and each defining one of the electrodes.

18. The apparatus as defined in claim 9, wherein the electrodes are interdigitating electrodes.

\* \* \* \* \*